(12) United States Patent
Kumar et al.

(10) Patent No.: US 7,297,712 B2
(45) Date of Patent: Nov. 20, 2007

(54) CATIONIC AMPHIPHILES FOR INTRACELLULAR DELIVERY OF THERAPEUTIC MOLECULES AND ITS COMPOSITION, PROCESS AND METHOD OF TREATMENT

(75) Inventors: Majeti Bharat Kumar, Hyderabad (IN); Arabinda Chaudhuri, Hyderabad (IN); Yerramsetti Ramadas, Hyderabad (IN); Nalam Madhusudhana Rao, Hyderabad (IN)

(73) Assignee: Council of Scientific and Industrial Research, New Delhi (IN)

( * ) Notice: Subject to any disclaimer, the term of this patent is extended or adjusted under 35 U.S.C. 154(b) by 860 days.

(21) Appl. No.: 10/106,849

(22) Filed: Mar. 27, 2002

(65) Prior Publication Data

US 2003/0190348 A1 Oct. 9, 2003

(51) Int. Cl.
C07D 207/04 (2006.01)
A61K 31/40 (2006.01)
A61K 47/22 (2006.01)
(52) U.S. Cl. ............ 514/424; 514/424; 514/425; 548/541
(58) Field of Classification Search .......... 548/541; 514/424, 425
See application file for complete search history.

(56) References Cited

U.S. PATENT DOCUMENTS 2,748,143 A * 5/1956 Erickson ............... 548/579
5,665,879 A * 9/1997 Heath et al. ............ 544/358
5,698,721 A * 12/1997 Heath ..................... 554/80
5,705,655 A * 1/1998 Heath et al. .......... 548/350.1
6,333,433 B1 * 12/2001 Banerjee et al. ......... 564/296
6,346,546 B1 * 2/2002 Bernardon et al. ...... 514/532

OTHER PUBLICATIONS

Fujii, Tashikazu et al, 'Dyeable polyurethane leather substitutes' CA 86:56247 (1977).*
Tanaka, Katsuhiko et al, 'Toners for electrostatic image development' CA 107:68042 (1987).*
Desimore, John A. et al, 'Cationic surfactants for potentiating the salt taste of food and for reducing the salt content thereof' CA 111:132908 (1989).*
Svitel, Juraj et al, 'Composite biosensor for sulfite assay. Use of water-insoluble hexacyanoferrate(III) salts as electron-transfer mediators' CA 129:257226 (1998).*
Zeng, 'Solid-liquid chiral phase transfer catalytic alkylation synthesis of (−)-2-ethoxycarbonyl-2-nonylcyclopentanone' CA 120:133888 (1994).*
Zeng, 'Alkylation catalyzed by chiral phase transfer reaction' CA 124:55396 (1995).*

* cited by examiner

*Primary Examiner*—James O. Wilson
*Assistant Examiner*—John Mabry
(74) *Attorney, Agent, or Firm*—Crowell & Moring LLP

(57) ABSTRACT

The present invention provides novel cationic amphiphiles capable of facilitating transport of biologically active molecules into cells wherein the said amphiphiles contain cyclic head group having polar functional groups and pharmaceutical composition useful for delivering biologically active therapeutic molecules into body cells.

22 Claims, 3 Drawing Sheets

Figure 1:
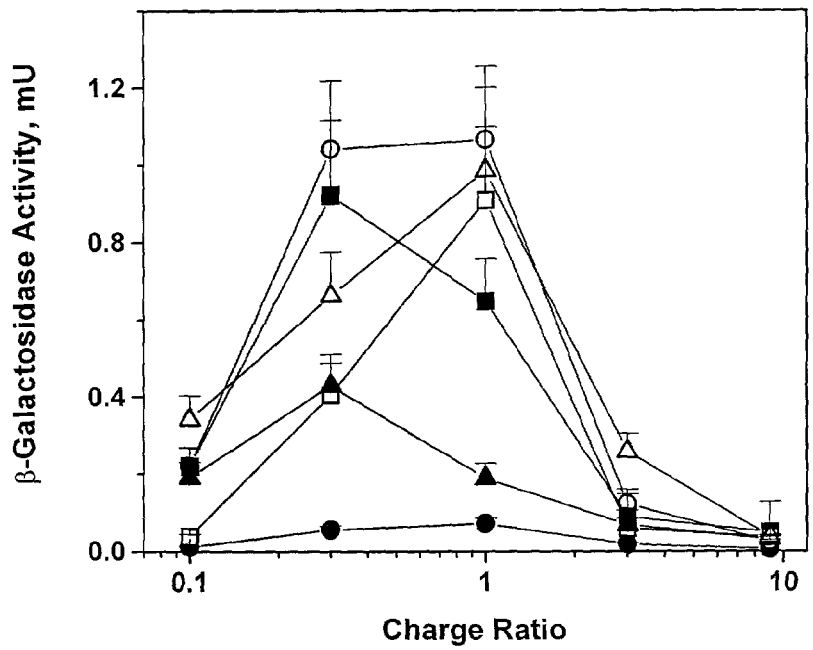

Figure 1. Transfection efficiencies of lipids 1-5 in COS-1 cells using cholesterol as the colipid (at 1:1 mole ratio of lipid to cholesterol) at different lipid to DNA charge ratios. The transfection efficiencies of the lipids 1 (●), 2 (○), 3 (■), 4 (□) and 5 (▲) were compared with that DMRIE (Δ).

Figure 2:
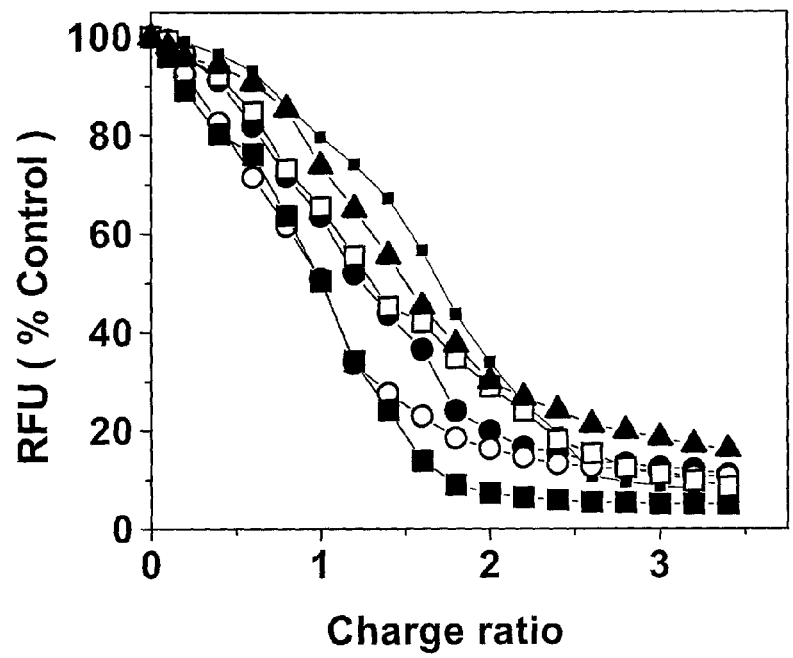

Figure 2. EtBr exclusion from lipid-DNA comlex. Decrease in fluorescence of EtBr was used to assess the interaction of DNA with lipids 1-5. DNA : EtBr complex was titrated with increasing amounts of lipid . Fluorescence in the absence of lipid was taken to be 100. Lipids: 1 (●), 2 (○), 3 (■), 4 (□) and 5 (▲)

Figure 3:
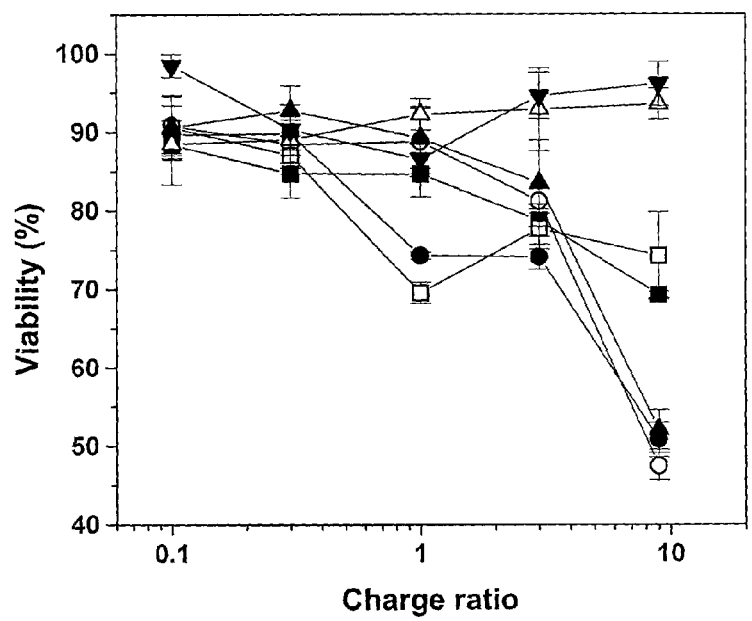

Figure 3. Cytotoxicity (viability) of lipids 1-5 on COS-1 cells using MTT assay. The absorption obtained with reduced formazon with cells in the absence of lipids was taken to be 100. Lipids: 1 (●), 2 (○), 3 (■), 4 (□), 5 (▲), Lipofectamine (Δ), DMRIE, (▼)

CATIONIC AMPHIPHILES FOR INTRACELLULAR DELIVERY OF THERAPEUTIC MOLECULES AND ITS COMPOSITION, PROCESS AND METHOD OF TREATMENT

FIELD OF THE INVENTION

The present invention relates to novel cationic amphiphiles containing cyclic head group. The present invention also relates to a pharmaceutical composition comprising said cationic amphiphiles, useful for the delivery of biologically active therapeutic molecules into body cells/tissues of mammals and humans.

BACKGROUND OF THE INVENTION

Although many defective genes associated with numerous genetic diseases have been identified and characterized, because of the selective permeability of biological cell membranes, delivering required amounts of therapeutically important genes into the target body cells is often a daunting challenge.

Thus, success of gene therapy approach in treating genetic diseases depends, in a major way, on the development of efficient and safe gene delivery reagents that will facilitate the intracellular delivery of therapeutic genes into the particular body cells of a patient. Accordingly, development of safe and efficient gene delivery reagents and methods that can facilitate entry of functional genes into body cells are of great medical importance. Amphiphilic molecules containing both polar and non-polar regions in their molecular architecture have been used in delivering therapeutically important molecules into cells. This makes sense given the existence of both polar and non-polar segments in biological cell membranes. Cationic amphiphiles are the particularly important class of amphiphilic compounds used most extensively for enhancing intracellular delivery of many biologically active therapeutic compounds. Broadly speaking, at physiological pH the polar segment of cationic amphiphile interacts with the therapeutically important molecules including polyanionic macromolecular DNA, RNA, proteins etc. while the non-polar region of the cationic amphiphiles facilitate the passage of the therapeutic compounds through the non-polar part of the cell membranes.

The following references are examples of cationic amphiphiles that are known in the art to be useful for enhancing the intracellular delivery of therapeutically important molecules. In addition to the molecular structures, these prior arts contain useful information and discussion on the properties of the cationic amphiphiles those are believed to be responsible for their carrier properties.

Felgner et al., *Proc.Natl.Acad.Sci. U.S.A.*, 84, 7413-7417 (1987), reported the first use of a highly efficient cationic lipid N-[1-(2,3-dioleyloxy)propyl]-N,N,N-trimethyl ammonium chloride(DOTMA) as the DNA transfection vector.

U.S. Pat. Nos. 4,897,355 and 4,946,787 (1990) reported the synthesis and use of N-[.omega..(.omega.-1)-dialky-loxy]-and N-[.omega..(.omega.-1)-dialkenyloxy]-alk-1-yl-N,N,N-tetrasubstituted ammonium amphiphiles and their pharmaceutical formulation as efficient transfection vectors.

Leventis, R. and Silvius, J. R *Biochim. Biophys. Acta.* 1023, 124-132, (1990) reported the interactions of mammalian cells with lipid dispersions containing novel metabolizable cationic amphilphiles.

U.S. Pat. No. 5,264,618 (1993) reported the synthesis and use of additional series of highly efficient cationic lipids for intracellular delivery of biologically active molecules.

Felgner et al. *J.Biol.Chem.* 269, 2550-2561 (1994) reported enhanced gene delivery and mechanistic studies with a novel series of cationic lipid formulations.

U.S. Pat. No. 5,283,185 (1994) reported the synthesis and use of 3β[N-($N^1$,$N^1$-dimethylaminoethane)carbamoyl]cholesterol, termed as "DC-Chol"for delivery of a plasmid carrying a gene for chloramphenicol acetyl transferase into cultured mammalian cells.

U.S. Pat. No. 5,283,185 (1994) reported the use of N-[2-[[2,5-bis[(3-aminopropyl)amino]-1-Oxopentyl]aminoet-hyl]-N,N-dimethyl-2,3-bis-(9-octadecenyloxy)-1-Propanaminium tetra(trifluoroacetate), one of the most widely used cationic lipids in gene delivery. The pharmaceutical formulation containing this cationic lipid is sold commercially under the trade name "Lipofectamine".

Solodin et al. *Biochemistry* 34,13537-13544, (1995) reported a novel series of amphilic imidazolinium compounds for in vitro and in vivo gene delivery.

Wheeler et al. *Proc. Natl. Acad.Sci. U.S.A* 93, 11454-11459, (1996) reported a novel cationic lipid that greatly enhances plasmid DNA delivery and expression in mouse lung.

U.S. Pat No. 5,527,928 (1996) reported the synthesis and the use of N,N,N,N-tetramethyl-N,N-bis(hydroxyethyl)-2,3-di(oleolyoxy)-1,4-butanediammonim iodide i.e pharmaceutical formulation as transfection vector.

U.S. Pat. No. 5,698,721 (1997) reported the synthesis and use of alkyl O-phosphate esters of diacylphosphate compounds such as phosphatidylcholine or posphatidylethanolamine for intracellular delivery of macromolecules.

U.S. Pat. Nos. 5,661,018; 5,686,620 and 5,688,958 (1997) disclosed a novel class of cationic phospholipids containing phosphotriester derivatives of phosphoglycerides and sphingolipids efficient in the lipofection of nucleic acids.

U.S. Pat. No. 5,614,503 (1997) reported the synthesis and use of an amphiphatic transporter for delivery of nucleic acid into cells, comprising an essentially nontoxic, biodegradable cationic compound having a cationic polyamine head group capable of binding a nucleic acid and a cholesterol lipid tail capable of associating with a cellular membrane.

U.S. Pat. No. 5,705,693 (1998) disclosed the method of preparation and use of new cationic lipids and intermediates in their synthesis that are useful for transfecting nucleic acids or peptides into prokaryotic or eukaryotic cells. These lipids comprise one or two substituted arginine, lysine or ornithine residues, or derivatives thereof, linked to a lipophilic moiety.

U.S. Pat. No. 5,719,131 (1998) has reported the synthesis of a series of novel cationic amphiphiles that facilitate transport of genes into cells. The amphiphiles contain lipophilic groups derived from steroids, from mono or dialkylamines, alkylamines or polyalkylamines.

U.S. Pat. No. 5,527,928, (1996) reported on the synthesis and transfection biology of a novel cationic lipid namely, N,N,N',N'-tetramethyl-N,N'-bis (2-hydroxyethyl)-2,3-di (oleoyloxy)-1,4-butaneammonium iodide.

OTHER PUBLICATIONS

Behr, J. P., Demeneix, B., Loeffler, J. P. and Perex-Mutul, J. *Proc. Natl. Acad. Sci. USA*, 1989, 86, 124-132.
Levantis, R., and Silvius, J. R. *Biochim. Biophys. Acta.*, 1990, 1023, 124-132.

Gao, X. and Huang, L. *Biochim. Biophys. Res. Commun.*, 1991, 179, 280-285.

Akao, T., Nakayama, T., Takeshia, K. and Ito, A., *Biochem. Mol. Biol. Int.*, 1994, 34, 915-920.

Felgner, J. H.; Kumar, R.; Sridhar, C. N.; Wheeler, C. J.; Tsai, Y-J.; Border, R.; Ramsey, P.; Martin, M.; Felgner, P. L. *J. Biol. Chem.*, 1994, 269, 2550-2561.

Wheeler, C. J.; Felgner, P. L.; Tsai, Y. J.; Marshall, J.; Sukhu, L.; Doh, S. G.; Hartikka, J.; Nietupski, J.; Manthorpe. M.; Nichols, M. *Proc. Natl. Acad. Sci. USA.* 1996, 93, 11454-11459.

Bennett, M. J.; Aberle, A. M.; Balasubramaniam, R. P.; Malone, J. G.; Malone, R. W.; Nantz, M. H. *J. Med. Chem.* 1997, 40, 4069-4078.

Blessing, T.; Remy, J.-S.; Behr, J.-P.; *J. Am. Chem. Soc.*, 1998, 120, 8519-8520.

Wang, J.; Guo, X.; Xu, Y.; Barron, L.; Szoka, F. C., *J. Med. Chem,* 1998, 41, 2207-2215

Lim, Y.; Choi, Y. H.; Park, J. *J. Am. Chem. Soc.*, 1999, 121, 5633-5639.

Lim, Y.; Kim, C.; Kim, K.; Kim, S. W.; Park, J. *J. Am. Chem. Soc.*, 2000, 122, 6524-6525.

Zhu, J.; Munn, R. J.; Nantz, M. H. *J. Am. Chem. Soc.*, 2000, 122, 2645-2646.

Vandenburg, Y. R.; Smith, B. D.; Perez-Payan, N.; Davis, A. P.; *J. Am. Chem. Soc.*, 2000, 122, 3252-3253.

Lynn, D. M.; Langer, R.; *J. Am. Chem. Soc.*, 2000, 122, 10761-10768.

Ferrari, M. E.; Rusalov, D.; Enas, J.; Wheeler, C. J.; *Nuc. Acid. Res.* 2001, 29, 1539-1548.

Banerjee, R.; Das, P. K.; Srilakshmi, G. V.; Chaudhuri, A.; Rao, N. M. *J. Med. Chem.*1999, 42, 4292-4299.

Banerjee, R.; Mahidhar, Y. V.; Chaudhuri, A.; Gopal, V.; Rao, N. M. *J. Med. Chem.* 2001, 44, 4176-4185.

Singh, S. R.; Mukherjee, K.; Banerjee, R.; Chaudhuri, A.; Hait, S. K.; Moulik, S. P.; Ramadas, Y.; Vijayalakshmi, A.; Rao, N. M. *Chem. Eur. J.* (in press).

Floch, V.; Bolc'h, G. Le.; Gable-Guillaume, C.; Bris, N. Le.; Yaouanc, J-J.; Abbayes, H. Des.; Fe'rec, C.; Cle'ment, J-C. *Eur. J. Med. Chem.*, 1998, 33, 923-934.

Solodin, I.; Brown, C.; Bruno, M.; Chow, C.; Jang, E-H.; Debs, R.; Heath, T. *Biochemistry,* 1995, 34, 13537-13544.

OBJECTS OF THE INVENTION

The main object of the invention is to provide novel cationic amphiphilic compounds containing polar cyclic head group.

Another object of the invention is to provide novel cationic amphiphilic compounds, which are useful for delivering therapeutically effective amounts of biologically active molecules into cells/tissues of mammals.

Yet another object of the invention is to provide cationic amphiphilic compounds in which a hydrophobic group is directly linked to the positively charged Nitrogen atom, which is itself in the cyclic ring containing two hydroxyl groups.

Still another object of the invention is to provide novel cationic amphiphilic compounds without any glycerol backbone in their structure.

Another object of the invention is to provide novel therapeutic formulation comprising one or more of the cationic amphiphilic compounds of the invention.

It is a further object of the invention to provide therapeutic formulation useful in gene therapy and delivery of biologically active molecules into cells/tissues of mammals.

SUMMARY OF THE INVENTION

The present invention relates to novel cationic amphiphilic compounds that facilitate the intracellular delivery of biologically active (therapeutic) molecules. The present invention also relates to pharmaceutical compositions comprising such cationic amphiphiles those are useful for delivering biologically active therapeutic molecules into body cells. The novel cationic lipids of the present invention are particularly useful to combat genetic diseases by non-viral gene therapy.

DETAILED DESCRIPTION OF THE INVENTION

The present invention provides for a bioactive cationic amphiphile represented by a general formula (I).

FORMULA (I)

wherein;

$R^1$ and $R^2$ independently represent hydrogen atom or lipophilic moiety excluding the possible definition for $R^1$ and $R^2$ being simultaneously as hydrogen atom;

$R^3$ and $R^4$ independently represent hydrogen or a polar group;

n=1, 2 or 3;

X=an inorganic or organic anion.

The present invention also provides a bioactive cationic amphiphile as represented by general formula (II)

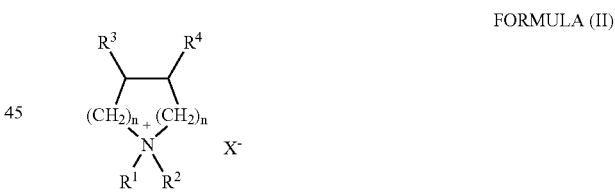

FORMULA (II)

Wherein $R_1$, $R_2$, $R_3$ and $R_4$ independently or in combination represented as described below:

n=1

$R_1 = R_2 = CH_3-(CH_2)_{10}CH_2-$, $CH_3-(CH_2)_{12}CH_2-$, $CH_3-(CH_2)_{14}CH_2-$, $CH_3-(CH_2)_{16}CH_2-$ and/or $CH_3-(CH_2)_7-CH=CH(CH_2)_7CH_2$.

$R_3 = R_4 =$ hydroxyl group.

An embodiment of the present invention, wherein X is selected from halogen atom, tosyl group and acetate group.

Yet another embodiment of the present invention, wherein $R^1$ is hydrogen and $R^2$ is $C_{8-22}$ saturated alkyl group or an unsaturated alkyl group having one to three unsaturation.

Still another embodiment of the present invention, wherein $R^1$ is $C_{8-22}$ alkyl group saturated or unsaturated alkyl group having one to three unsaturation and $R^2$ is hydrogen atom or $C_{8-22}$ saturated or unsaturated alkyl group having one to three double unsaturation.

Further embodiment of the present invention, wherein $R^3$ and $R^4$ are independently represented by any combination of groups selected from hydrogen, hydroxy, hydroxy alkyl, and amino or primary amine.

Still another embodiment of the present invention, wherein hydroxy alkyl and primary amine consists of 1-5-carbon atoms.

Yet another embodiment of the present invention, wherein $R^1$ independently represents a hydrogen atom and $R^2$ is represented by $C_{8-22}$ carbon atoms selected from saturated alkyl or unsaturated alkyl chain having one to three double bonds.

Still another embodiment of the present invention, wherein $R^1$ represents $C_{8-22}$ carbon atoms selected from saturated alkyl or unsaturated alkyl chain having one to three double bonds and R2 independently represents a hydrogen atom.

Yet another embodiment of the present invention, wherein both $R^1$ and $R^2$ are represented by $C_{8-22}$ carbon atoms selected from saturated alkyl or unsaturated alkyl chain having one to three double bonds.

Still another embodiment of the present invention, wherein said compound having a hydrophobic group is directly linked to the positively charged Nitrogen atom, which by itself is a part of cyclic ring containing polar substituted groups.

The present invention also provides for a pharmaceutical composition for intracellular delivery of biologically active molecules, said composition comprising:
 at least a cationic amphiphile;
 a bioactive molecule;
 a colipid; and
 optionally an additive.

An embodiment of the present invention, a pharmaceutical composition wherein the bioactive cationic amphiphile used to facilitate the intracellular delivery of bioactive molecules having the following structural formula:

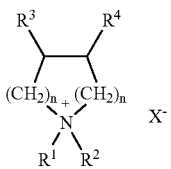

FORMULA (I)

wherein;
 $R^1$ and $R^2$ independently represent hydrogen atom or lipophilic moiety excluding the possible definition for $R^1$ and $R^2$ being simultaneously a hydrogen atom;
 $R^3$ and $R^4$ independently represent hydrogen or a polar group;
 n=1, 2 or 3;
 X=an inorganic or organic anion.

Yet another embodiment of the present invention, a pharmaceutical composition wherein the bioactive molecule is selected from the group consisting of ribosomal RNA, antisense polynucleotide of DNA or RNA, polynucleotide of genomic DNA, cDNA or mRNA that encodes for therapeutically important protein, nucleic acid, an oligonucleotide and a peptide.

Still another embodiment of the present invention, a pharmaceutical composition wherein the nucleic acid is circular, lineal plasmid or RNA.

Further embodiment of the present invention, a pharmaceutical composition wherein the colipid is selected from the group consisting of cholesterol, phosphatidylethanolamine, phosphatidylglycerol.

Still another embodiment of the present invention, a pharmaceutical composition according to claim 10 wherein the preferred range of cationic amphiphile and colipid is in the ratio of 1:0-1:2.5.

Yet another embodiment of the present invention, a pharmaceutical composition wherein said composition administered comprises an effective amount of DNA in the range of 0.1-0.5 μg with regard to 50.000 cells of an in vitro system.

Still another embodiment of the present invention, a pharmaceutical composition wherein said composition can be administered intravenously, intramuscularly and intraperitonially. Yet another embodiment of the present invention, a pharmaceutical composition wherein said additives are selected from physiologically acceptable additives.

Further embodiment of the present invention, a pharmaceutical composition wherein said additives are used to stabilize the formulation and for the effective delivery of bio active molecule.

Still another embodiment of the present invention, a pharmaceutical composition wherein said composition can be formulated with lipophilic therapeutic anti cancer agents selected from doxorubicin, paclitaxel, docetaxel and 5-fluorouracil.

Yet another embodiment of the present invention, a pharmaceutical composition wherein said composition is formulated with viral agents selected from Acyclovir.

Still another embodiment of the present invention, a pharmaceutical composition wherein said composition is formulated with antibiotics selected from amphotericin B.

Further embodiment of the present invention, a pharmaceutical composition wherein said composition is formulated with an anti-influenza agent to deliver to the lung, the primary site of the infection.

The present invention also provides a process for the preparation of bioactive cationic amphiphiles of formulae (I-II) said process comprising the steps of:
 (a) coupling an appropriate saturated or unsaturated lipophilic aliphatic bromide with saturated or unsaturated lipophilic aliphatic alkyl amine in polar aprotic solvents in presence of base to obtain the corresponding aliphatic hydrophobic secondary amine;
 (b) protecting both the terminal primary alcohol groups of an aliphatic alcohols containing additional polar functionalities with suitable protecting groups in polar aprotic solvent;
 (c) reacting the secondary amine obtained in step (a) with the primary hydroxyl protected aliphatic polar intermediate obtained in step (b) in polar aprotic solvents in presence of an organic base to obtain quaternized amphiphile compound;
 (d) passing the quaternized amphiphilic compound obtained in step (c) through anion-exchange column chromatography and eluting with a mixture of polar organic solvent to obtain the required cationic amphiphile.

An embodiment of the present invention, a process wherein the aliphatic saturated alkyl bromide is elected from the group consisting of 10-30 carbon atoms.

Yet another embodiment of the present invention, a process wherein the aliphatic saturated alkyl amine is selected from the group consisting of 10-30 carbon atoms.

Further embodiment of the present invention, a process wherein the substituted primary hydroxyl group as claimed in step (c) is selected from the group consisting of hydroxyl, hydroxy alkyl, amino or a primary amino and most preferably hydroxyl or amino.

Further embodiment of the present invention, a process wherein the amino group is protected with t-boc, f-moc or any other suitable protective agents.

Still another embodiment of the present invention, a process wherein the aliphatic unsaturated alkyl amine used is selected from the group consisting of 10-30 carbon atoms.

Yet another embodiment of the present invention, a process wherein the polar aprotic solvents in which the reaction is carried out is selected from the group comprising dimethyl formamide, dimethylsulphoxide, pyridine, triethyl amine.

Further embodiment of the present invention, a process wherein the reaction is carried out in the presence of weak base selected from inorganic alkali metal carbonates.

Yet another embodiment of the present invention, a process wherein the primary alcohol protection group is selected from tosyl chloride, mesyl chloride, and the like.

Still another embodiment of the present invention, a process wherein the polar aprotic solvent used in step (a) is selected from dimethyl sulphoxide, N,N-dimethyl formamide, ethyl acetate, tetrahydrofuran and the like.

Yet another embodiment of the present invention, a process wherein the reaction of step (a) is carried out at a temperature between 50° C. to 100° C.

Still another embodiment of the present invention, a process wherein the protection of terminal primary hydroxyl groups of step (b) is carried out at a temperature between −10° C. to 50° C.

Further embodiment of the present invention, a process wherein primary alcohol is selected from erythrytol or its homologues.

Yet another embodiment of the present invention, a process wherein the polar aprotic solvent used in step (c) is selected from dimethyl sulphoxide, N,N-dimethyl formamide, ethyl acetate, tetrahydrofuran.

Further embodiment of the present invention a process wherein the organic base used in step (c) is selected from triethyl amine, pyridine, piperidine.

Yet another embodiment of the present invention, a process wherein the reaction of step (c) is carried out at a temperature between 50° C. to 100° C.

Still another embodiment of the present invention, a process wherein the anion-exchange resin used in step (d) is selected from resin having chloride or bromide ion available for exchange.

Yet another embodiment of the present invention, a process wherein the organic solvent used as ingredients of the polar eluent in step (d) is selected from methanol, ethanol, chloroform, dichloro methane, ethyl acetate.

The present invention further provides for a method for intracellular delivery of biologically active molecules said method comprising administering to a subject at least one biologically active compound represented by the following structural formula:

FORMULA (I)

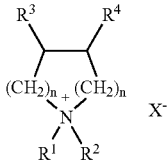

wherein;

R$^1$ and R$^2$ independently represent hydrogen atom or lipophilic moiety excluding the definition of R$^1$ and R$^2$ being simultaneously represented as hydrogen atom;

R$^3$ and R$^4$ independently represent hydrogen or a polar group;

n=1, 2, 3 or 4;

X=an inorganic or organic anion.

An embodiment of the present invention, a method wherein the subject is selected from humans and other species including murine, feline, bovine, equine and ovine or non-human primate species.

Another embodiment of the present invention, a method wherein said method is used to combat genetic diseases by non-viral gene therapy.

Still another embodiment of the present invention, a method wherein said composition can be administered intravenously, intramuscularly and intraperitonially.

Yet another embodiment of the present invention, a method wherein cytotoxicities are minimal and the cell viability more than 80%.

Yet another embodiment of the present invention, wherein said method is used to construct cell lines for gene therapy applications in said subjects.

The present invention is also further explained in the form of preferred embodiments.

The distinctive novel structural features common to the cationic amphiphiles disclosed in the present invention include:

(1) The presence of hydrophobic groups which are directly linked to the positively charged nitrogen atom;

(2) The positively charged nitrogen atom is part of the cyclic head group; and (3) Unlike many other commercially available glycerol-backbone based cationic amphiphiles used in delivering genes into cells, the presently disclosed cationic lipids do not have any glycerol-backbone in their molecular architectures. It is believed that these unique structural features contribute significantly to the increased gene delivery efficiencies of the cationic amphiphiles disclosed herein.

According to the practice of the present invention, "cationic" means the positive charge is either on quaternized nitrogen and/or on a protonated substituent of the cyclic head group. The cationic characters of the present amphiphiles may contribute to the enhanced interaction of the amphiphiles with biologically active molecules such as nucleic acids and/or with cell constituents such as plasma membrane glycoproteins. Such enhanced interaction between the cationic amphiphiles and therapeutically active biological macromolecules and/or cell membrane constituents may play a key role in successfully transporting the therapeutic molecules into the cells.

The invention cationic lipids have a lipophilic domain that facilitates the formation of lipid complexes or aggregates in aqueous solutions. The lipophilicity of the hydrophobic domains and the hydrophilicity of the polar head group domains are such that when the cationic lipids are confronted with aqueous solutions, lipid aggregates are formed in the presence or absence of a second compound. Exemplary lipophilic R$_1$ and R$_2$ groups include (1) saturated C$_8$-C$_{22}$ alkyl groups and (2) unsaturated C$_8$-C$_{22}$ alkyl groups containing one to three unsaturation.

In one preferred embodiment of the presently disclosed cationic lipids where n=1, both R$_1$ and R$_2$ are selected from C$_8$-C$_{22}$ saturated alkyl groups, both R$_3$ and R$_4$ are independently represented in any combination of groups selected from hydrogen, hydroxyl, hydroxy alkyl, amino or primary amine and X$^-$ is selected from chloride or bromide ions.

Syntheses of the Cationic Lipids

Scheme I outlines the synthetic strategy employed for preparing the cationic lipids of the present invention containing a five member cyclic head groups (n=1 in generic Structure of formula (I). The same synthetic scheme is employed to synthesize cationic lipids with seven and nine member cyclic head groups (n=2 and 3 respectively, in generic Structure of formula (I).

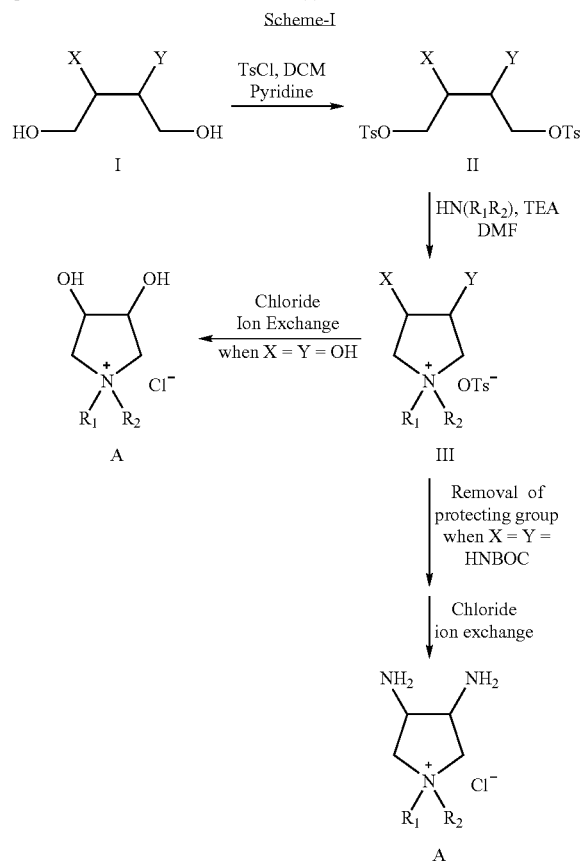

Scheme-I

Both the primary hydroxyl groups of the starting alcohol is first converted to their tosyl derivative by reacting them with p-toluenesulfonyl chloride in presence of pyridine as a base. The resulting di-tosyl derivative (the intermediate II in Scheme I) is then subjected to reaction with the appropriate secondary amine in polar aprotic solvent like N.N-dimethyl formamide to form the cationic amphiphile (III), a tosylate counterion containing analog of the present cationic lipids. A final treatment of the intermediate III with chloride ion-exchange resins affords the target cationic amphiphile (I) of the present invention. As shown in Scheme I, to synthesize cationic lipids with two hydroxyl functionalities in the cyclic head group, protecting the secondary hydroxyl group of the starting material is not necessary. However, to prepare cationic amphiphiles with two amino functionalities in the cyclic head group, execution of Scheme I requires protection of both the primary amino group of the starting material and a later deprotection step.

Formulations

The invention also provides novel therapeutic formulation comprising therapeutically effective amounts of the cationic amphiphilic compounds disclosed herein, biologically active molecules and co-lipids. One or more additional physiologically acceptable substances may be included in the pharmaceutical formulation of the invention to stabilize the formulation for storage or to facilitate successful intracellular delivery of the biologically active molecules. Co-lipids according to the practice of the present invention are useful in mixing with one or more cationic amphiphiles. Cholesterol is an excellent co-lipid for use in combination with the presently described cationic lipids to facilitate successful intracellular delivery of the biologically active molecules. A preferred range of molar ratio of cationic amphiphile to co-lipid is 1:0 to 1:2.5. As such, it is within the art to vary the said range to a considerably wide extent.

Biologically active molecules that can be administered intracellularly in therapeutic amounts using the cationic amphiphilic compound of the present invention include ribosomal RNA, antisense polynucleotide of RNA or DNA, polynucleotide of genomic DNA, cDNA or mRNA that encodes for a therapeutically important protein. The cationic amphiphiles of the present invention may be blended such that one or more of the representatives thereof are used in a combination to facilitate entry of the said biologically active molecules into cells/tissues.

According to the present invention, the amphiphiles are used either in pure form or in combination with other lipids or helper lipids such as cholesterol, phosphatidylethanolamine, phosphatidylglycerol, etc. The said therapeutic formulation can be stored at 0° C.-4° C. until complexed with the biologically active therapeutic molecules. Agents that prevent bacterial growth and increase the shelf life may be included along with reagents that stabilize the preparation, e.g., low concentrations of glycerol. It is specifically warned that freezing and thawing cycles could cause loss in efficiency of the formulation.

The present invention also provides for various formulations that facilitate intracellular delivery of biologically active molecules.

The present invention also provides for a formulation of cationic amphiphiles and nucleic acid may be administered intravenously besides other routes such as intramuscular and intra peritonial. Further, the said formulation of amphiphiles may be administered to cells at a ratio of 0.1-0.5 microgram of DNA to 50,000 cells in an in vitro system. The amount of amphiphile could be varied from a lipid to DNA charge ratio of 0.1 to 10, considering one positive charge for one amphiphile molecule to one negative charge of a nucleotide base.

The plasmid used is a construct of an Cyto Megalo Virus promoter linked to a reporter egene β-galactosidase as supplied by Gibco BRL Life Technologies, USA (cat no.10586-014)The plasmid could be of any construction and the example given is merely to demonstrate the efficiency of the amphiphilic formulation. Similar examples of plasmid include PGL-2 and PGL-3 of Promega and others.

The invention further provides a process for the preparation of the said formulation comprising the steps of preparing a dispersion of a cationic amphiphile disclosed in the present invention; contacting said dispersion with a biologically active molecule to form a complex between said amphiphiles and said molecules and contacting cells with said complex thereby facilitating transfer of said biologically active molecules into the cells.

Cellular Cytotoxicities of the Amphiphiles Disclosed in the Invention

The viabilities of cells in presence of various cationic amphiphiles disclosed herein were checked according to the standard protocol described in "Animal Cell Culture, $2^{nd}$ Edition. Ed. I. R. L. Press, Oxford University Press (1977)". The transfection efficiencies of the cationic lipids were studied in the range of 0-10 nmole and within this limit, the cell cytotoxicities were observed to be minimal and the cell viabilities were determined to be more than 80%. The cationic amphiphiles were used with varying mole ratios of lipid to DNA using cholesterol as the neutral co-lipid.

Applications

The process of the present invention can be exploited for preparing cationic transfection lipids with polar cyclic head groups. The invention lipids are useful for delivering polyanions, polypeptides or nucleopolymers into cells. The cationic lipids disclosed herein can be used to deliver an expression vector into a cell for manufacturing or therapeutic use. The expression vectors can be used in gene therapy protocols to deliver a therapeutically useful protein to a cell or for delivering nucleic acids encoding therapeutically useful protein molecules that can generate an immune response in a host for vaccine or other immunomodulatory purposes according to the known methods. The vector-transformed cell can be used to produce commercially useful cell lines, such as a cell line for producing therapeutic proteins or enzymes (e.g. erythropoietin), growth factors (e.g. human growth hormone, G-CSF or interleukins) or other proteins.

The invention lipid-nucleic acid complexes can be used to construct cell lines for gene therapy applications in subjects such as humans or other species including murine, feline, bovine, equine, ovine or non-human primate species. The invention lipids can be used in presence of serum and will thus deliver polyanions into cells in tissue culture medium containing serum in vitro or in animal in vivo.

The invention lipids complexed with nucleopolymers can be used in antisense inhibition of gene expression in a cell by delivering an antisense oligonucleotide into the cell. A cell that is blocked for expression of a specific gene(s) is useful for manufacturing and therapeutic applications. Exemplary manufacturing uses include inhibiting protease synthesis in a cell to increase production (i.e., reduce target protein degradation caused by the protease) of a protein for a therapeutic or diagnostic application. Exemplary therapeutic applications include inhibiting synthesis of cell surface antigens (histocompatibility antigens, such as MHC class II genes, and the like) to reduce rejection and/or to induce immunologic tolerance of the cell after it is implanted into a subject or when the cell is transfected in vivo.

The invention lipids can be formulated with anionic, zwitterionic and lipophilic therapeutic agents including anticancer agents such as doxorubicin, a lipophilic compound, to obtain complexes comprising the invention lipids and a therapeutic agent(s). The invention lipids can be formulated with known antiviral agents such as HPMPC (9-(3-hydroxy-2-phosphonylmethoxy)propyl)cytosine), PMEA(9-(2-phosphonylmethoxy)ethyl)adenine), PMEG PMEA (9-(2-phosphonylmethoxy)ethyl)guanine), PMPA (9-(2-phosphonylmethoxy)propyl)adenine), AZT, 3TC, and their derivatives to obtain lipid complexes with antiviral agents. The invention lipids can be formulated with polyene antibiotics such as amphotericin B. Such formulations are useful for delivering the therapeutic agents into the cytoplasm of cells in vitro or in vivo. Complexes consisting of an invention cationic lipid and an anti-influenza agent can be used to deliver the antiviral agent to the lung, the primary site of infection. These complexes can be prepared by any of the techniques now known or subsequently developed for preparing lipid complexes containing therapeutic agents.

BRIEF DESCRIPTION OF THE ACCOMPANYING DRAWINGS

FIG. 1 summarizes the in vitro gene delivery efficiencies for the cationic amphiphiles 1-5 disclosed in the present invention and that of DMRIE, one of the most widely used commercially available transfection lipids under certain conditions and FIG. 2 shows some representative lipid:DNA interactions for cationic amphiphiles 1-5 disclosed in the present invention.

FIG. 3 provides the in vitro cellular toxicity data of the cationic amphiphiles 1-5 disclosed in the present invention.

EXAMPLES

The following examples are given by way of illustration of the present invention and therefore should not be construed to limit the scope of the present invention. Synthetic procedures for representative cationic amphiphiles 1-5 disclosed in the present invention are described in the following examples 1-5. The structures of cationic lipids 1-5 are shown below.

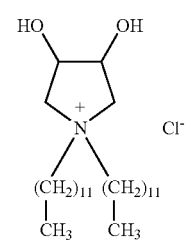

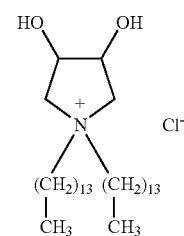

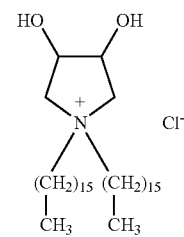

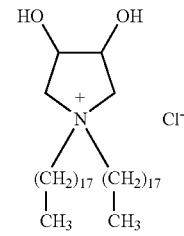

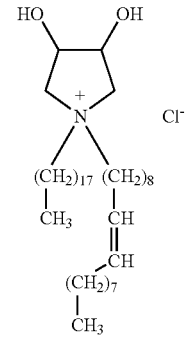

Example 1

Synthesis of N,N-di-n-dodecyl-3,4-dihydroxy pyrrolidinium chloride (amphiphile 1)

Step (a). To 5 g n-dodecyl amine (27 mmol) dissolved in 10 ml DMSO, 6.7 g of n-dodecyl bromide (27 mmol), and 3.7 g of potassium carbonate (27 mmol) were added. The mixture was kept under stirring for 24 hours at 80° C. The reaction mixture was taken in chloroform 100 ml and washed with water (2×150 ml), the chloroform layer was dried over anhydrous sodium sulfate and filtered. Chloroform was removed from the filtrate on a rotary evaporator and column chromatographic purification (using 60-120 mesh size silica) of the residue using 1-2% methanol in chloroform as an eluent afforded (3.4 g, yield 35%) of the desired intermediate secondary amine, namely, N,N-di-n-dodecylamine.

Step (b). To erythritol (4 g 33.9 mmol) dissolved in 100 ml dry pyridine, tosyl chloride (11.6 g, 61 mmol), a few crystals of DMAP were added. The mixture was kept under stirring for 1 h at −5° C. Pyridine was removed on a rotary evaporator and column chromatographic purification (using 60-120 mesh size silica) of the residue using 25-30% ethyl acetate in pet-ether (v/v) as the eluent provided of crude title compound 7 g. Pure ditosylate intermediate was obtained (4 g, 27.4% yield) by final recrystallization of the crude product from chloroform:pet-ether (4:6, 25 ml).

Step (c). Reacting the purified ditosylate (0.5 g, 1.2 mmol) with 5 equivalent of secondary amine of step (a) (2.0 g, 5.8 mmol) in triethyl amine 40 ml at 80° C. for 72 hours. Silica gel column chromatographic purification was performed using 60-120 mesh size silica and 10-15% methanol in chloroform as the eluent. Crude title amphiphile No.1 was obtained by subjecting the quaternized salt to repeated treatment (3 times) with chloride ion-exchange resin, each time using a freshly generated Amberlyst A-26 chloride ion exchange column and about methanol 75 ml as the eluent. Finally, pure quaternized title amphiphile salt 1 (0.08 g, 14.5% yield) was obtained by crystallizing the crude product using chloroform:pet-ether 10 ml 3:7. All the isolated intermediates gave spectroscopic data in agreement with their assigned structures.

$^1$H-NMR of amphiphile 1 (200 MHz, CDCl$_3$): δ/ppm=0.9 [6H, t, 2×-C$\underline{H}_3$]; 1.20-1.45 [36H, m, 18×-C$\underline{H}_2$]; 1.5-1.8 [4H, m, 2×-C$\underline{H}_2$]; 3.4-3.6 [8H, m, —N—C$\underline{H}_2$]; 4.05-4.2 [2H, m, —C$\underline{H}$—OH]; 4.75-4.8 [1H, m, —CH—O$\underline{H}$]; 5.5-5.6 [1H, m, —CH—O$\underline{H}$].

Example 2

Procedure for the Preparation of N,N-di-n-tetradecyl-3,4-dihydroxy pyrrolidinium chloride (Amphiphile No. 2).

Step (a). To 5 g n-tetradecyl amine (23.4 mmol) dissolved in 10 ml DMSO, 6.4 g of n-tetradecyl bromide (23.4 mmol),and 3.2 g of potassium carbonate (23.4 mmol) were added. The mixture was kept under stirring for 24 hours at 80° C. The reaction mixture was taken in 100 ml chloroform and washed with water (2×150 ml), the chloroform layer was dried over anhydrous sodium sulfate and filtered. Chloroform was removed from the filtrate on a rotary evaporator and column chromatographic purification (using 60-120 mesh size silica) of the residue using 1-2% methanol in chloroform as the eluent afforded 3.4 g (35% yield) of the desired intermediate secondary amine, namely, N,N-di-n-tetradecylamine.

Step (b). To 4 g of erythritol (33.9 mmol) dissolved in 100 ml dry pyridine, tosyl chloride 11.6 g, (61 mmol), a few crystals of DMAP were added. The mixture was kept under stirring for 1 h at −5° C. Pyridine was removed on a rotary evaporator and column chromatographic purification (using 60-120 mesh size silica) of the residue using 25-30% ethyl acetate in pet-ether (v/v) as the eluent provided 7 g of crude title compound. Pure ditosylate intermediate was obtained (4 g, 27.4% yield) by final recrystallization of the crude product from 25 ml 4:6 (v/v) chloroform:pet-ether.

Step (c). Reacting the purified ditosylate (0.5 g, 1.2 mmol) with 5 equivalent of secondary amine (2.4 g, 5.8 mmol) in 40 ml triethyl amine at 80° C. for 72 hours. Silica gel column chromatographic purification was performed using 60-120 mesh size silica and 10-15% methanol in chloroform as the eluent. Crude title amphiphile No.1 was obtained by subjecting the quaternized salt to repeated (3 times) chloride ion-exchange column chromatography, each time using a freshly generated Amberlyst A-26 chloride ion exchange column and about 75 ml of methanol as the eluent. Finally, pure quaternized title amphiphile salt 2 (0.06 g, 9.7% yield) was obtained by crystallizing the crude product using 10 ml 3:7 (v/v) chloroform:pet-ether. All the isolated intermediates gave spectroscopic data in agreement with their assigned structures.

$^1$H-NMR of amphiphile 2 (200 MHz, CDCl$_3$):δ/ppm=0.9 [6H, t, 2×-C$\underline{H}_3$]; 1.20-1.45 [48H, m, 24×-C$\underline{H}_2$]; 3.4-3.75 [8H, m, 4×N—C$\underline{H}_2$]; 4.05-4.20 [2H, m, 2×-C$\underline{H}$—OH]; 4.75-4.80 [1H, m, —CH—O$\underline{H}$]; 5.5-5.6 [1H, m, —CH—O$\underline{H}$].

Example 3

Procedure for the Preparation of N,N-di-n-hexadecyl-3,4-dihydroxy pyrrolidinium chloride (Amphiphile No. 3).

Step (a). To 5 g n-hexadecyl amine (20.7 mmol) dissolved in 10 ml DMSO, 6.3 g of n-hexadecyl bromide (20.7 mmol),and 2.9 g of potassium carbonate (20.7 mmol) were added. The mixture was kept under stirring for 24 hours at 80° C. The reaction mixture was taken in 100 ml chloroform and washed with water (2×150 ml), the chloroform layer was dried over anhydrous sodium sulfate and filtered. Chloroform was removed from the filtrate on a rotary evaporator and column chromatographic purification (using 60-120 mesh size silica) of the residue using 1-2% methanol in chloroform as the eluent afforded 3.4 g (35% yield) of the desired intermediate secondary amine, namely, N,N-di-n-hexadecylamine.

Step (b). To 4 g of erythritol (33.9 mmol) dissolved in 100 ml dry pyridine, tosyl chloride 11.6 g, (61 mmol), a few crystals of DMAP were added. The mixture was kept under stirring for 1 h at −5° C. Pyridine was removed on a rotary evaporator and column chromatographic purification (using 60-120 mesh size silica) of the residue using 25-30% ethyl acetate in pet-ether (v/v) as the eluent provided 7 g of crude title compound. Pure ditosylate intermediate was obtained (4 g, 27.4% yield) by final recrystallization of the crude product from 25 ml 4:6 (v/v) chloroform:pet-ether.

Step (c). Reacting the purified ditosylate (0.5 g, 1.2 mmol) with 5 equivalent of secondary amine (2.7 g, 5.8 mmol) in 40 ml triethyl amine at 80° C. for 72 hours. Silica gel column chromatographic purification was performed using 60-120 mesh size silica and 10-15% methanol in chloroform as the eluent. Crude title amphiphile No.1 was obtained by subjecting the quaternized salt to repeated (3 times) chloride ion-exchange column chromatography, each time using a freshly generated Amberlyst A-26 chloride ion exchange column and about 75 ml of methanol as the eluent. Finally, pure quaternized title amphiphile salt 3 (0.13 g, 17.3% yield) was obtained by crystallizing the crude product using 10 ml 3:7 (v/v) chloroform:pet-ether. All the isolated intermediates gave spectroscopic data in agreement with their assigned structures.

$^1$H-NMR of amphiphile 3 (200 MHz, CDCl$_3$): δ/ppm=0.90 [6H, t, 2×-C$\underline{H}_3$]; 1.20-1.80 [56H, m, 28×-C$\underline{H}_2$]; 3.40-3.75 [8H, m4×-N—C$\underline{H}_2$]; 4.05-4.20 [2H, m, 2×-C$\underline{H}$—OH]; 4.75-4.80 [1H, m, —CH—O$\underline{H}$]; 5.5-5.6 [1H, m, —CH—O$\underline{H}$].

Example 4

Procedure for the Preparation of N,N-di-n-octadecyl-3,4-dihydroxy pyrrolidinium chloride (Amphiphile No. 4).

Step (a). To 5 g n-octadecyl amine (18.5 mmol) dissolved in 10 ml DMSO, 6.2 g of n-octadecyl bromide (18.5 mmol),and 2.6 g of potassium carbonate (18.5 mmol) were added. The mixture was kept under stirring for 24 hours at 80° C. The reaction mixture was taken in 100 ml chloroform and washed with water (2×150 ml), the chloroform layer was dried over anhydrous sodium sulfate and filtered. Chloroform was removed from the filtrate on a rotary evaporator and column chromatographic purification (using 60-120 mesh size silica) of the residue using 1-2% methanol in chloroform as the eluent afforded 3.6 g (37% yield) of the desired intermediate secondary amine, namely, N,N-di-n-octadecylaamine.

Step (b). To 4 g of erythritol (33.9 mmol) dissolved in 100 ml dry pyridine, tosyl chloride 11.6 g, (61 mmol), a few crystals of DMAP were added. The mixture was kept under stirring for 1 h at −5° C. Pyridine was removed on a rotary evaporator and column chromatographic purification (using 60-120 mesh size silica) of the residue using 25-30% ethyl acetate in pet-ether (v/v) as the eluent provided 7 g of crude title compound. Pure ditosylate intermediate was obtained (4 g, 27.4% yield) by final recrystallization of the crude product from 25 ml 4:6 (v/v) chloroform:pet-ether.

Step (c). Reacting the purified ditosylate (0.5 g, 1.2 mmol) with 5 equivalent of secondary amine (3.0 g, 5.8 mmol) in 40 ml triethyl amine at 80° C. for 72 hours. Silica gel column chromatographic purification was performed using 60-120 mesh size silica and 10-15% methanol in chloroform as the eluent. Crude title amphiphile No.4 was obtained by subjecting the quaternized salt to repeated (3 times) chloride ion-exchange column chromatography, each time using a freshly generated Amberlyst A-26 chloride ion exchange column and about 75 ml of methanol as the eluent. Finally, pure quaternized title amphiphile salt 4 (0.08 g, 10.7% yield) was obtained by crystallizing the crude product using 10 ml 3:7 (v/v) chloroform:pet-ether. All the isolated intermediates gave spectroscopic data in agreement with their assigned structures.

$^1$H-NMR of amphiphile 4 (200 MHz, CDCl$_3$): δ/ppm=0.90 [6H, 5, 2×-C$\underline{H}_3$]; 1.20-1.45 [64H, m, 32×-C$\underline{H}_2$]; 3.40-3.75 [8H, m, 4×-N—C$\underline{H}_2$]; 4.05-4.20 [2H, m, 2×-C$\underline{H}$—OH]; 4.75-4.8 [1H, m, —CH—O$\underline{H}$]; 5.5-5.6 [1H, m, —CH—O$\underline{H}$].

Example 5

Procedure for the Preparation of N-n-octadecyl-N-oleyl-3,4 dihydroxy pyrrolidinium chloride (Amphiphile No. 5).

Step (a). To 5 g oleyl amine (18.7 mmol) dissolved in 10 ml DMSO, 6.2 g of octadecyl bromide (18.7 mmol),and 2.6 g of potassium carbonate (18.7 mmol) were added. The mixture was kept under stirring for 24 hours at 80° C. The reaction mixture was taken in 100 ml chloroform and washed with water (2×150 ml), the chloroform layer was dried over anhydrous sodium sulfate and filtered. Chloroform was removed from the filtrate on a rotary evaporator and column chromatographic purification (using 60-120 mesh size silica) of the residue using 1-2% methanol in chloroform as the eluent afforded 2.7 g (27.8% yield) of the desired intermediate secondary amine, namely, N-n-octadecyl-N-oleyl amine.

Step (b). To 4 g of erythritol (33.9 mmol) dissolved in 100 ml dry pyridine, tosyl chloride 11.6 g, (61 mmol), a few crystals of DMAP were added. The mixture was kept under stirring for 1 h at −5° C. Pyridine was removed on a rotary evaporator and column chromatographic purification (using 60-120 mesh size silica) of the residue using 25-30% ethyl acetate in pet-ether (v/v) as the eluent provided 7 g of crude title compound. Pure ditosylate intermediate was obtained (4 g, 27.4% yield) by final recrystallization of the crude product from 25 ml 4:6 (v/v) chloroform:pet-ether.

Step (c). Reacting the purified ditosylate (0.5 g, 1.2 mmol) with 4 equivalent of secondary amine (2.4 g, 4.7 mmol) in 40 ml triethyl amine at 80° C. for 72 hours. Silica gel column chromatographic purification was performed using 60-120 mesh size silica and 10-15% methanol in chloroform as the eluent. Crude title amphiphile No.4 was obtained by subjecting the quaternized salt to repeated (3 times) chloride ion-exchange column chromatography, each time using a freshly generated Amberlyst A-26 chloride ion exchange column and about 75 ml of methanol as the eluent. Finally, pure quaternized title amphiphile salt 5 (0.05 g, 7.1% yield) was obtained by crystallizing the crude product using 10 ml 3:7 (v/v) chloroform:pet-ether. All the isolated intermediates gave spectroscopic data in agreement with their assigned structures.

$^1$H-NMR of amphiphile 5 (200 MHz, CDCl$_3$): δ/ppm=0.90 [6H, t,×2-C$\underline{H}_3$]; 1.20-1.45 [56H, m, 28×-C$\underline{H}_2$]; 1.90-2.00 [4H, m, 2×-CH═CH—C$\underline{H}_2$]; 3.40-3.75 [8H, m, 4×-N—C$\underline{H}_2$]; 4.05-4.20 [2H, m, —C$\underline{H}$—OH]; 4.75-4.80 [1H, m, —CH—O$\underline{H}$]; 5.20-5.40 [1H, m, —CH—O$\underline{H}$].

Example 6

Cell Transfection. COS-1 cells were seeded at a density of 15,000 cells/well in a 96-well plate eighteen hours before the transfection. 0.15 μg of plasmid DNA was complexed with varying amount of lipid (0.05-4.3 nmoles) in 13 μl of plain DMEM medium for 30 min. The charge ratios were varied from 0.1:1 to 9:1 (+/−) over this range of the lipid. The complex was diluted to 100 μl with plain DMEM and added to the wells. After 3 h of incubation, 100 μl of DMEM with 10% FCS was added to the cells. The medium was changed to 10% complete medium after 24 h and the reporter gene activity was estimated after 48 h. The cells were washed twice with PBS and lysed in 50 μl of lysis buffer (0.25 M Tris.HCl, pH 8.0 and 0.5% NP40). Care was taken to ensure complete lysis. The β-galactosidase activity per well was estimated by adding 50 μl of 2× substrate solution (1.33 mg/ml of ONPG, 0.2 M sodium phosphate, pH 7.15 and 2 mM magnesium chloride) to the lysate in a 96-well plate. Absorption at 405 nm was converted to β-galactosidase units by using calibration curve constructed with pure commercial β-galactosidase enzyme. The values of β-galactosidase units in replicate plates assayed on the same day varied by less than 30%. The transfection efficiency values reported were average values from four replicate transfection plates assayed on the same day. Each transfection experiment was repeated three times on three different days and the day-to-day variation in average transfection efficiency values for identically treated replicate transfection plates was 2-3 fold and was dependent on the cell density and conditions of the cells. FIG. 1 shows representative transfection results obtained with cationic lipids 1-5. As shown in FIG. 1, the in vitro transfection efficiency of cationic lipid 2 is comparable to or better than that of DMRIE, one of the most extensively used commercially available cationic transfection lipids used in in vitro gene delivery.

Example 7

Lipid:DNA Interactions Assay. Intercalation-induced fluorescence increase and competition with cationic lipids to bind to DNA has made Ethidium Bromide (EtBr) an excellent tool to study cationic lipid-DNA interactions. To assess the representative lipid:DNA interactions for the cationic lipids of the present invention, we have titrated the EtBr: pCMV β-gal complex with increasing amounts of cationic lipids 1-5.

The extent of Et.Br binding to the DNA was monitored by the changes in the fluorescence. EtBr fluorescence was monitored in Hitachi 4500 fluorimeter by setting the excitation wavelength at 518 nm and emission wavelength at 585 nm. To one ml of TE buffer (pH 8.0), 0.78 nmoles of DNA and 2.5 nmoles of EtBr were added. The change in fluorescence was monitored after adding small volumes of lipids 1-5 to the EtBr:DNA complex. Arbitrary fluorescence values were recorded after allowing sufficient time for equilibration. The order of addition of EtBr or lipid to DNA did not alter the final values indicating that the equilibrium does not depend on the order of addition and reaches in minutes. Percent fluorescence was calculated considering the fluorescence value in the absence of lipid as 100.

The data in FIG. 2 shows that lipids 1, 4 and 5 interact poorly with DNA as seen by their relatively poor ability to exclude ethidium bromide from DNA. Lipids 2 and 3 interact with DNA equally well up to lipid:DNA ratio of 1.25 or so (FIG. 2). The decrease in EtBr fluorescence at charge ratios of 3:1 was greater than 80% with all the lipids 1-5. Taken together the transfection results shown in FIG. 1 and the lipid:DNA interaction profiles shown in FIG. 2, it seems that strong lipid:DNA interactions for the presently described cationic lipids results into better intracellular gene delivery.

Example 8

Toxicity Assays. An MTT based viability assay was performed to assess the cytotoxicity of lipids 1-5 at various lipid:DNA charge ratios with COS-1 cells as described previously (Banerjee, R. et al. 1999). Except lipid 1, all the other lipids (2-5) showed least cytotoxicity even at a 9:1 lipid:DNA charge ratio (FIG. 3). For lipids 1, 4 and 5 at a 3:1 charge ratio the toxicity varied from 15-25% of the treated cells. The toxicity of lipid 2 (with shorter alkyl chains) may originate from its probable detergent-like cell-lysing activity. As shown in FIG. 3, the cellular toxicity profiles of lipids 2-5 of the present invention are better than those of several commercially available cationic transfection lipids including lipofectin, lipofectAmine and DMRIE.

Advantages
1. The novel cationic lipids of the present invention are particularly useful to combat genetic diseases by non-viral gene therapy.
2. The cationic amphiphiles of the present invention do not have glycerol-backbone in their molecular structures.
3. The cationic amphiphiles are useful for delivering polyanions, polypeptides and nucleopolymers into cells.

What is claimed is:
1. A bioactive cationic amphiphile as represented by a general formula (I);

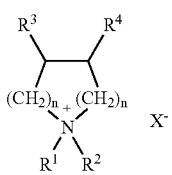

FORMULA (I)

wherein:
$R_1$, $R_2$, $R_3$ and $R_4$ are independently represented as described below:
n=1
$R_1=R_2=CH_3—(CH_2)_{10}CH_2—$, $CH_3—(CH_2)_{12}CH_2—$, $C_3—(CH_2)_{14}CH_2—$, $CH_3—$, $(CH_2)_{16}CH_2—$ or $CH_3—(CH_2)_7—CH=CH(CH_2)_7CH_2—$;
$R_3=R_4=$hydroxyl group;
$X^-=$an inorganic or organic anion.

2. A compound according to claim 1 wherein X is selected from the group consisting of halogen atom, tosyl group and acetate group.

3. A bioactive cationic amphiphile represented by a general formula (I):

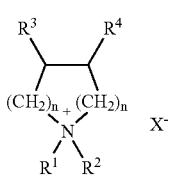

FORMULA (I)

wherein;
n=1;
both $R^1$ and $R^2$ are $C_{12-18}$ saturated alkyl groups;
$R^3=R^4=$hydroxyl group;
X=an inorganic or organic anion.

4. A bioactive cationic amphiphile represented by a general formula (I)

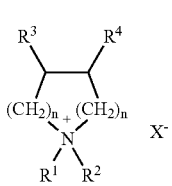

FORMULA (I)

wherein;
$R^1$ and $R^2$ independently represent a hydrogen atom or a $C_{12-18}$ saturated or unsaturated alkyl group excluding the definition of $R^1$ and $R^2$ being simultaneously represented as a hydrogen atom;

R³ and R⁴ independently represent hydrogen or a hydroxyl group wherein R³ and R⁴ are not simultaneously hydrogen;
n=1;
X=an inorganic or organic anion.

5. A process for the preparation of bioactive cationic amphiphiles of formula (I):

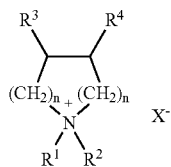

FORMULA (I)

wherein:
$R_1$, $R_2$, $R_3$ and $R_4$ are independently represented as described below:
n=1
$R_1=R_2=CH_3—(CH_2)_{10}CH_2—$, $CH_3—(CH_2)_{12}CH_2—$, $CH_3—(CH_2)_{14}CH_2—$, $CH_3—$, $(CH_2)_{16}CH_2—$ and/or $CH_3—(CH_2)_7—CH=CH(CH_2)_7CH_2—$;
$R_3=R_4$=hydroxyl group;
X⁻=an inorganic or organic anion said process comprising:
(a) coupling a saturated or unsaturated aliphatic bromide with a saturated or unsaturated aliphatic alkyl amine in a polar aprotic solvent in the presence of a base to obtain the corresponding aliphatic hydrophobic secondary amine;
(b) protecting both the terminal primary alcohol groups of an aliphatic alcohol containing two additional secondary hydroxyl groups with protecting groups in a polar aprotic solvent;
(c) reacting the secondary amine obtained in step (a) with the protected primary hydroxyl aliphatic polar intermediate obtained in step (b) in a polar aprotic solvent in the presence of an organic base to obtain a quaternized amphiphilic compound;
(d) passing the quaternized amphiphilic compound obtained in step (c) through anion-exchange column chromatography and eluting with a mixture of polar organic solvents to obtain the cationic amphiphile.

6. A process as claimed in claim 5 wherein the saturated aliphatic bromide is an aliphatic saturated alkyl bromide containing 12-18 carbon atoms.

7. A process as claimed in claim 5 wherein the saturated aliphatic alkyl amine is an aliphatic saturated alkyl amine containing 12-18 carbon atoms.

8. A process as claimed in claim 5 wherein the unsaturated aliphatic alkyl amine is an aliphatic unsaturated alkyl amine containing 18 carbon atoms having one double bond.

9. A process as claimed in claim 5 wherein the amino group is protected with, tert-butyloxycarbonyl or 9-fluorenylmethyloxycarbonyl or any other protective agents.

10. A process as claimed in claim 5 wherein the polar aprotic solvent in which the reaction is carried out is selected from the group consisting of dimethyl formamide, dimethyl sulphoxide, pyridine, triethyl amine, and mixtures thereof.

11. A process as claimed in claim 5 wherein the reaction is carried out in the presence of an inorganic alkali metal carbonate.

12. A process as claimed in claim 5 wherein the primary alcohol protecting group is tosyl chloride or mesyl chloride.

13. A process as claimed in claim 5 wherein the polar aprotic solvent used in step (a) is selected from the group consisting of dimethyl sulphoxide, N,N-dimethyl formamide, ethyl acetate, and tetrahydrofuran.

14. A process as claimed in claim 5 wherein the reaction of step (a) is carried out at a temperature between 50° C. to 100° C.

15. A process as claimed in claim 5 wherein the protection of terminal primary hydroxyl groups of step (b) is carried out at a temperature between –10° C. to 50° C.

16. A process as claimed in claim 5 wherein the primary alcohol is erythrytol.

17. A process as claimed in claim 5 wherein the polar aprotic solvent used in step (c) is selected from the group consisting of dimethyl sulphoxide, N,N-dimethyl formamide, ethyl acetate, and tetrahydrofuran.

18. A process as claimed in claim 5 wherein the organic base used in step (c) is triethyl amine, pyridine or piperidine.

19. A process as claimed in claim 5 wherein the reaction of step (c) is carried out at a temperature between 50° C. to 100° C.

20. A process as claimed in claim 5 wherein the anion-exchange resin used in step (d) is a resin having a chloride or bromide ion available for ion exchange.

21. A process as claimed in claim 5 wherein the organic solvents used as ingredients of the polar eluent in step (d) are selected from the group consisting of methanol, ethanol, chloroform, dichloromethane, and ethyl acetate.

22. A bioactive cationic amphiphile represented by a general formula (I)

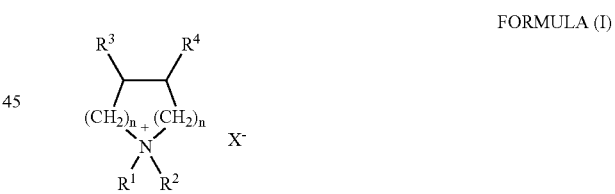

FORMULA (I)

wherein;
both R¹ and R² are an unsaturated $C_{18}$ alkyl groups having one unsaturation;
$R^3=R^4$=hydroxyl group;
n=1;
X=an inorganic or organic anion.

* * * * *